United States Patent
Tashiro et al.

(10) Patent No.: US 6,801,598 B2
(45) Date of Patent: Oct. 5, 2004

(54) RADIATION SENSING APPARATUS

(75) Inventors: Kazuaki Tashiro, Kanagawa (JP); Noriyuki Kaifu, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 75 days.

(21) Appl. No.: 10/277,033

(22) Filed: Oct. 22, 2002

(65) Prior Publication Data

US 2003/0086523 A1 May 8, 2003

(30) Foreign Application Priority Data

Oct. 23, 2001 (JP) ........................................ 2001-325167

(51) Int. Cl.$^7$ .............................................. H05G 1/64
(52) U.S. Cl. ................................ 378/98.8; 250/370.09; 250/205
(58) Field of Search ............................... 378/98.8, 98.2, 378/98.3, 98.12, 108, 368; 250/370.09, 368, 205, 221, 214 R, 208.1; 348/340

(56) References Cited

U.S. PATENT DOCUMENTS

| | | | | |
|---|---|---|---|---|
| 4,675,739 A | * | 6/1987 | Catchpole et al. | 378/98.8 |
| 4,769,710 A | * | 9/1988 | Uchida | 348/294 |
| 5,315,101 A | | 5/1994 | Hughes et al. | 250/208.1 |
| 5,512,942 A | * | 4/1996 | Otsuki | 348/143 |
| 5,693,948 A | | 12/1997 | Sayed et al. | 250/370.09 |
| 5,773,832 A | * | 6/1998 | Sayed et al. | 250/370.09 |
| 5,825,032 A | | 10/1998 | Nonaka et al. | 250/370.09 |
| 5,894,129 A | | 4/1999 | Pool | 250/370.09 |
| 6,178,224 B1 | * | 1/2001 | Polichar et al. | 378/98.2 |
| 6,333,963 B1 | | 12/2001 | Kaifu et al. | 378/98.2 |
| 6,476,394 B1 | * | 11/2002 | Amitani et al. | 250/368 |
| 6,539,076 B1 | * | 3/2003 | Shoji | 378/98.8 |
| 6,714,623 B2 | * | 3/2004 | Sako et al. | 378/98.8 |
| 2002/0024601 A1 | | 2/2002 | Kaifu et al. | 348/207 |
| 2002/0025022 A1 | | 2/2002 | Kaifu et al. | 378/97 |
| 2002/0051071 A1 | * | 5/2002 | Itano et al. | 348/340 |
| 2002/0159563 A1 | | 10/2002 | Tashiro et al. | 378/98.8 |
| 2003/0002624 A1 | * | 1/2003 | Rinaldi et al. | 378/98.8 |

FOREIGN PATENT DOCUMENTS

| | | |
|---|---|---|
| JP | 9-107503 | 4/1997 |
| JP | 11-99144 | 4/1999 |

* cited by examiner

Primary Examiner—Edward J. Glick
Assistant Examiner—Irakli Kiknadze
(74) Attorney, Agent, or Firm—Fitzpatrick, Cella, Harper & Scinto.

(57) ABSTRACT

A radiation sensing apparatus which includes a sensing unit for sensing a subject image to be obtained by irradiating a radiation from a radiation source to a subject, the sensing unit being capable of reading out non-destructively, and a detection circuit for detecting a start and/or a stop of irradiation of the radiation on a basis of a signal obtained from the sensing unit by the non-destructive read-out.

10 Claims, 11 Drawing Sheets

TO COMPARATOR

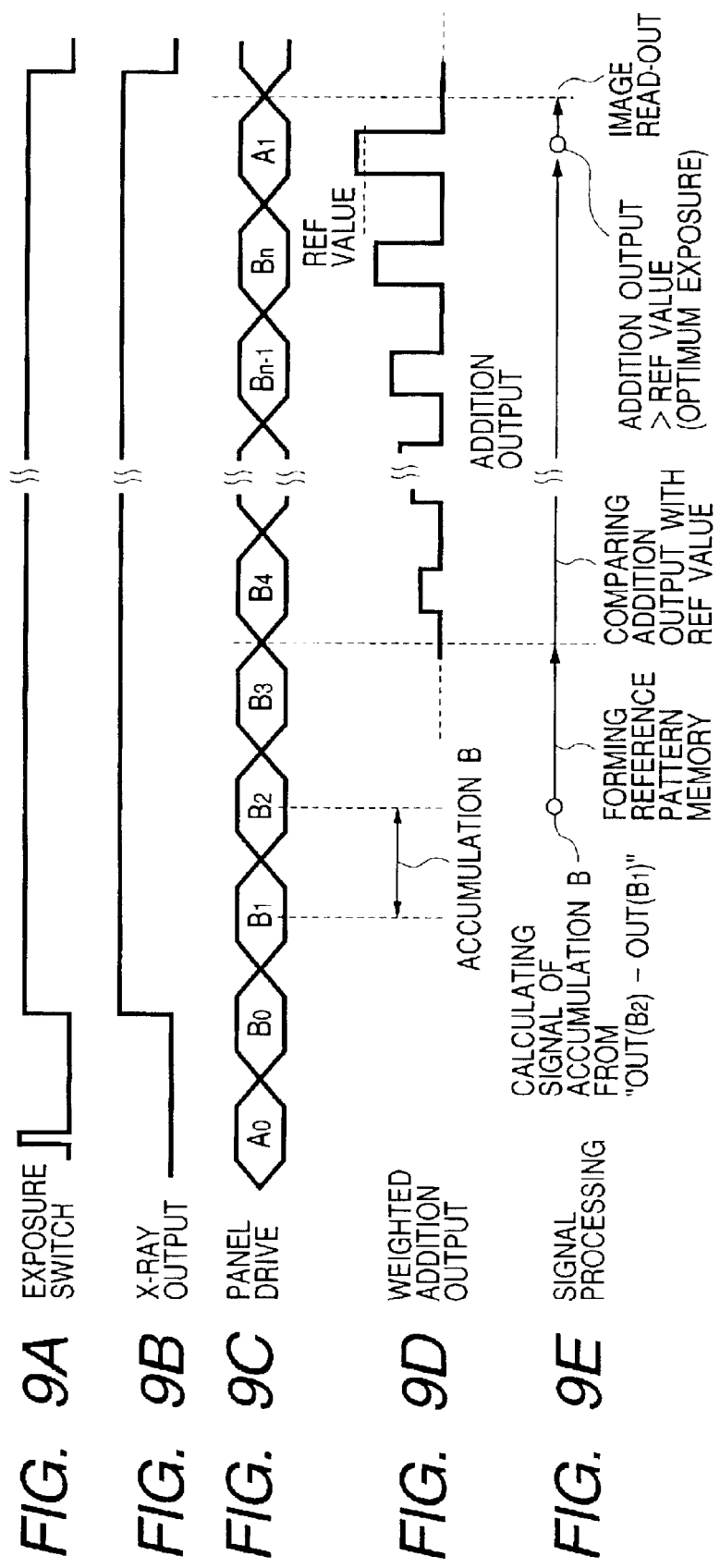

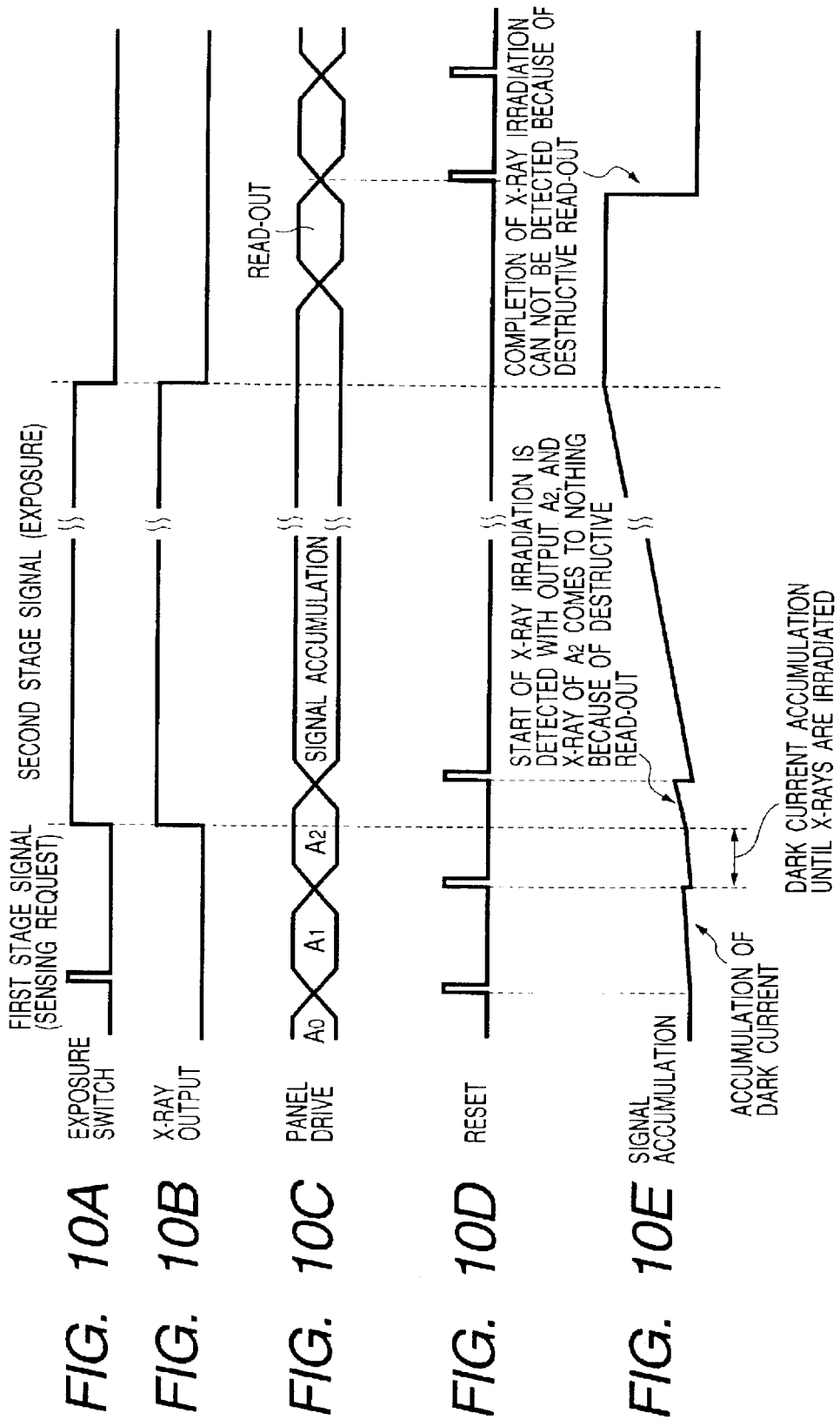

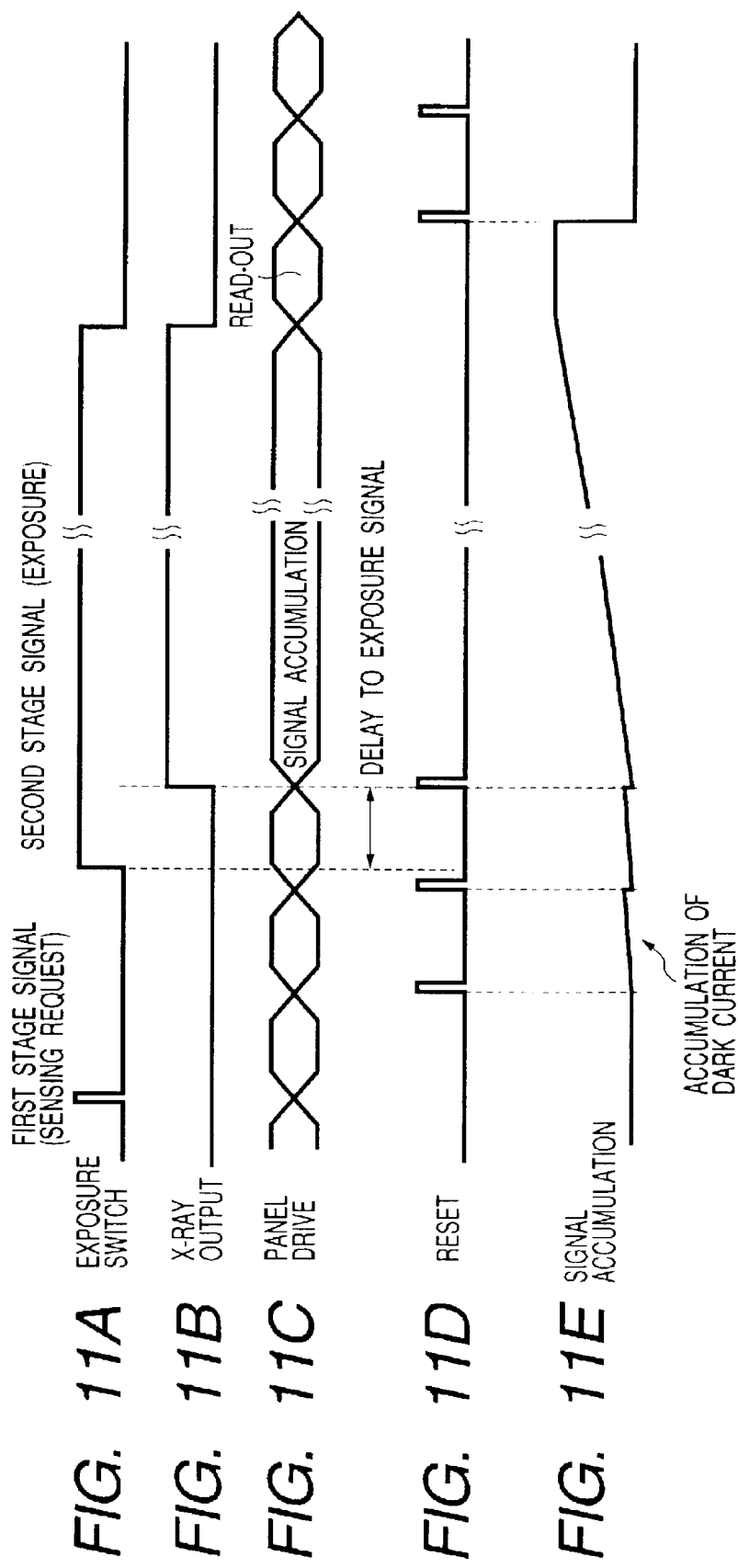

RADIATION SENSING APPARATUS

BACKGROUND OF THE INVENTION

1. Field of the Invention

The present invention relates to a radiation sensing apparatus to be used in radiation medical equipment and the like, and to a sensing method of the radiation sensing apparatus. For example, the present invention relates to a radiation sensing apparatus for performing an imaging diagnosis and the like using a high energy radiation such as an X-ray and a gamma ray, and to a sensing method of the radiation sensing apparatus.

2. Related Background Art

A method for obtaining a transmitted image of a subject by the use of a radiation having strong permeability such as an X-ray is generally used widely in a non-destructive examination for an industrial use and in a field of a medical diagnosis. Digitization has been advancing in various fields of medical treatments. In the field of the X-ray diagnosis, a two-dimensional digital X-ray highly sensitive transmission apparatus for sensing a visible light image with a TV camera after converting an input radiation into visible rays with a scintillator (fluorescent substance) and an image intensifier (I.I.) has been developed.

Furthermore, a radiation sensing apparatus using a charge coupled device (CCD) type image sensor or an amorphous silicon two-dimensional image sensor as sensing means in the place of the image intensifier (I.I.) to be combined with a fluorescent substance has recently been disclosed in U.S. Pat. No. 5,315,101, U.S. Pat. No. 5,693,948 and the like.

The following advantages can be cited as the advantages of the digital sensing apparatus to analog photography. For example, sensing without use of any film can be attained. The quantity of obtainable information can be increased by image processing. It is possible to make a database. Moreover, it is useful in a scene of an urgent medical treatment to be able to display a sensed image instantly at the scene.

Moreover, Japanese Laid-Open Patent Application No. 11-99144 discloses a flat panel type sensing apparatus applied to a movable X-ray sensing apparatus which can be moved to a bed side to perform X-ray sensing of a patient who has a difficulty of walking due to a serious injury or the like. Because the flat panel type sensing apparatus can easily be made to be small in size, it has also been considered to apply the flat panel type sensing apparatus to a portable type X-ray sensing apparatus for performing an urgent X-ray sensing at a scene of an accident.

Moreover, Japanese Laid-Open Patent Application No. 09-107503 discloses to apply a CCD type image sensor to an X-ray sensing apparatus for dental use or for mammography, in which a start of X-ray irradiation on the basis of an output of the image sensor can be detected without connecting the image sensor with an X-ray irradiation apparatus directly.

An example of a sensing sequence in case of detecting a start of X-ray irradiation on the basis of an output of an image sensor without connecting the image sensor with an X-ray irradiation apparatus directly will be explained by reference to FIGS. 10A to 10E. FIG. 10A shows an output signal of an exposure switch. FIG. 10B shows a state of irradiation of an X-ray. FIG. 10C shows a driving state of a CCD type image sensor. FIG. 10D shows reset signals. FIG. 10E shows a signal output.

The output signal of the exposure switch is a two-stage signal. A first stage of the signal is a sensing request signal. A second sage of the signal is an exposure signal. The CCD type image sensor starts its operation by a photographer's action of turning on a drive switch (not shown) separated from the X-ray irradiation apparatus. The photographer turns on the first stage exposure switch, and subsequently turns on the second stage exposure switch.

The CCD type image sensor performs its reset operation repeatedly until the image sensor detects X-ray irradiation, thereby waiting exposure while reading out a dark current periodically. In case of the CCD type image sensor, because accumulated electric charges are transferred to the outside to be read out at every read-out operation, only destructive read-out can be performed due to its configuration. The CCD type image sensor and the like have the characteristic of accumulating a dark current even in the state of no signal. Because the dark current is one of the causes of noises at the time of sensing a minute signal, a reset operation for decreasing the charges due to the dark current accumulated in the image sensor is required just before sensing for obtaining a useful subject signal. Naturally, the read-out accompanied by the reset operation is a destructive read-out. When X-ray irradiation is detected by the destructive read-out in a frame operation $A_2$ shown in FIG. 10C, signal accumulation due to the X-ray irradiation is started at a time of the completion of the reset operation of the frame.

However, the following two points become problems in the drive technique described above.

One of them is that useless exposure to an X-ray occurs. Because the signal in the frame in which the X-ray is detected is read out by the destructive read-out, the signal is not used for an image signal at all. In the worst case, the X-ray irradiation for the period of time of read-out of one frame becomes useless. Because an exposure dose should be suppressed to the utmost in an radiation sensing for a diagnosis having a medical object, it is desired to remove such uselessness.

Moreover, in such a destructive read-out, the end of the X-ray irradiation cannot be detected. Then, the read-out is performed by terminating signal accumulation after a pre-determined period of time set before sensing in advance by anticipating a time when the X-ray irradiation is ended. A dark current in the period of time from the termination of the X-ray irradiation to the read-out is a cause of noises, and causes a deterioration of the image quality of an obtained image.

Accordingly, in case of the sensing regarding the image quality and the exposure dose as important, a radiation irradiation apparatus and a radiation sensing apparatus are electrically connected with each other to synchronize the timing of an X-ray exposure between them by exchanging signals between them. To put it concretely, a reset operation (initialization operation) is started at a sensing request signal, and the reset operation is repeated while the radiation sensing apparatus is waiting an exposure signal. After the reset operation performed at the time of the recognition of the exposure signal is terminated, an exposure permission signal is transmitted to a generation apparatus. Consequently, the exposure of the radiation exposure apparatus, and a photographer as well, is limited in accordance with the reset timing.

An example of a sensing sequence of the above-described radiation sensing apparatus is described by reference to FIGS. 11A to 11E. FIG. 11A shows an output signal of an exposure switch; FIG. 11B shows the state of irradiation of an X-ray; FIG. 11C shows a driving state of a CCD type image sensor; FIG. 11D shows reset signals; and FIG. 11E shows a signal output.

The output signal of the exposure switch is a two-stage signal. A first stage of the signal is a sensing request signal. A second sage of the signal is an exposure signal. The radiation sensing apparatus starts its reset operation by recognizing the first stage output signal of the exposure switch. After that, the radiation sensing apparatus performs the reset operation repeatedly until the apparatus detects the second stage signal of the exposure switch to wait exposure while reading out a dark current periodically. When the radiation sensing apparatus detects the second stage signal of the exposure switch, the radiation sensing apparatus allows the radiation irradiation apparatus to expose at a time of the completion of the initialization at that time, and the radiation sensing apparatus starts signal accumulation.

However, the drive technique described above have the problems of the following two points.

One of them is the occurrence of the delay of real sensing to the exposure signal. Because the exposure should be allowed after the completion of the reset operation, with respect to the input timing of the exposure signal which the photographer expects, the exposure delays for the period of time of reading out one frame in the worst case. On the other hand, in the radiation sensing for a diagnosis having a medical object, it is desired to perform exposure and signal accumulation while escaping the breezing of a subject, the shaking of the body and the like. Consequently, it becomes important to perform radiation sensing at the instance when the photographer observing and controlling the subject wants to sense the subject. The above-mentioned delay of sensing to the exposure signal brings about to miss the optimum instance and to decrease the information of the subject.

The other one of them is a problem caused by the exchanges of signals between the apparatus for generating a radiation and the sensing apparatus. That is, a radiation irradiation apparatus using an X-ray film including a silver salt or the like is obliged to be remodeled for the signal exchanges, and it becomes necessary due to the installation of the image sensor to calibrate exposure timing to each radiation irradiation apparatus severally. This makes the installation very troublesome. In particular, there are many urgent cases which require the use of movable X-ray sensing apparatus or a portable X-ray sensing apparatus, and therefore it is required to eliminate such troublesomeness.

Consequently, it is desirable to make the signal connection between the radiation irradiation apparatus and the radiation sensing apparatus unnecessary, and to permit a photographer to expose at arbitrary sensing timing, and further to make it possible to obtain a signal at a high speed response.

SUMMARY OF THE INVENTION

An object of the present invention is to provide a radiation sensing apparatus which does not need signal connection between a radiation sensing unit and a radiation irradiating unit, and a sensing method of the radiation sensing apparatus.

A radiation sensing apparatus of an embodiment of the present invention for achieving the above-mentioned object comprises a sensing unit arranged to sense a subject image to be obtained by irradiating a radiation from a radiation source to a subject, the sensing unit being capable of reading out non-destructively, and a detection circuit arranged to detect a start and/or a stop of irradiation of the radiation on a basis of a signal obtained from the sensing unit by the non-destructive read-out.

Moreover, another embodiment of the present invention provides a sensing method of a radiation sensing apparatus including a sensing unit arranged to sense a subject image to be obtained by irradiating a subject with a radiation from a radiation source, the sensing unit being capable of reading out non-destructively, the method comprising a step of detecting a start and/or a stop of irradiation of the radiation on a basis of a signal obtained by the non-destructive read-out.

The other objects and features of the present invention will be clear in the following descriptions in the specification and the attached drawings.

BRIEF DESCRIPTION OF THE DRAWINGS

FIGS. 9A, 9B, 9C, 9D and 9E are timing charts for illustrating the operations of the embodiment of FIG. 6;

FIGS. 10A, 10B, 10C, 10D and 10E are timing charts for illustrating the operations of conventional X-ray sensing; and FIGS. 11A, 11B, 11C, 11D and 11E are timing charts for illustrating the operations of the other conventional X-ray sensing.

DESCRIPTION OF THE PREFERRED EMBODIMENTS

In the following, the preferred embodiments of the present invention are described in detail by reference to the attached drawings.

First Embodiment

Figure 1:
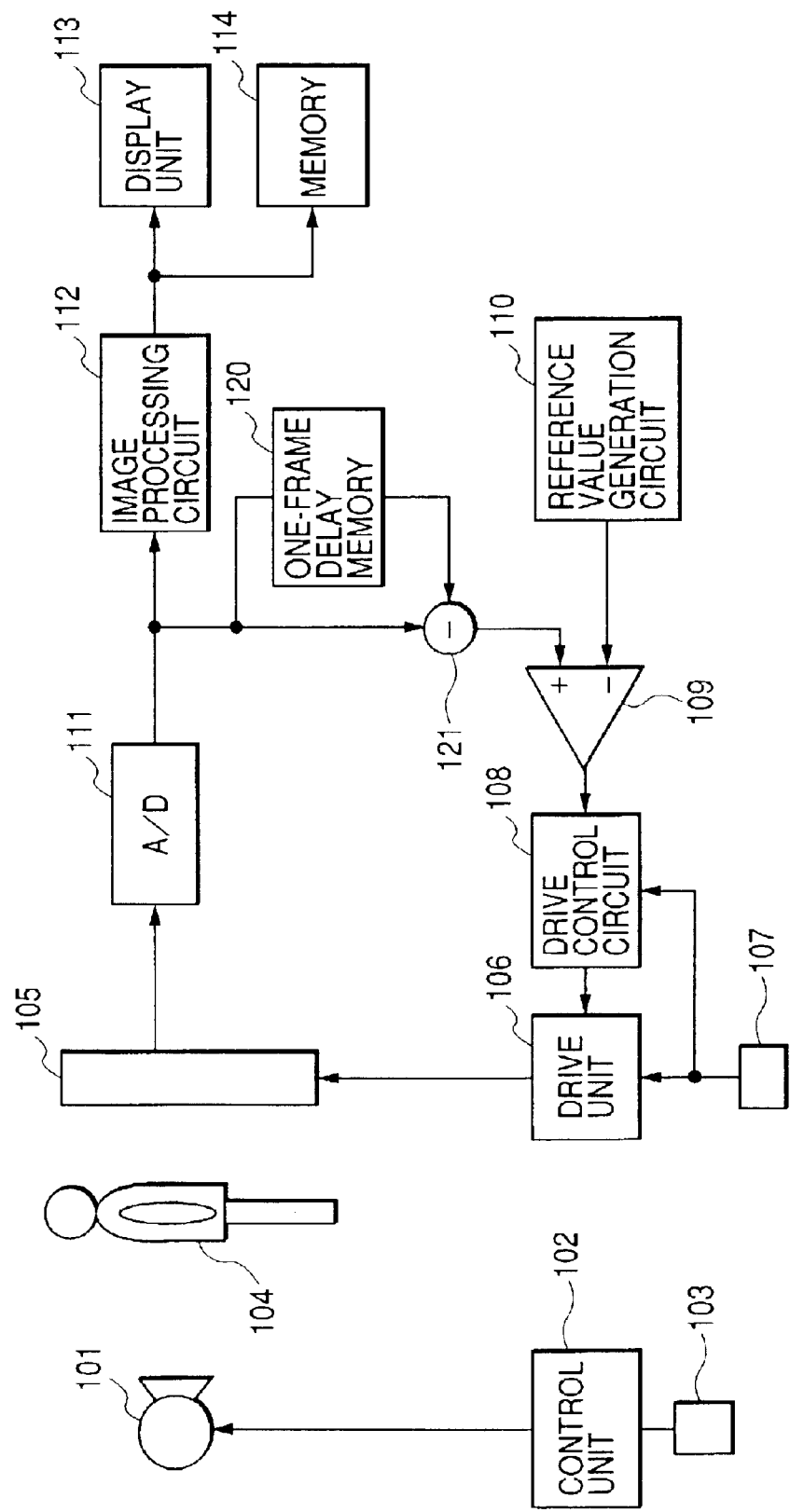
FIG. 1 is a block diagram showing the configuration of a first embodiment of the radiation sensing apparatus of the present invention.

FIG. 1 is a block diagram showing the configuration of a first embodiment of the radiation sensing apparatus of the present invention. First, it is supposed that still images of, for example, a lung, a stomach, a breast and the like of a human being are sensed in the present embodiment.

An X-ray irradiation apparatus composed of an X-ray source 101, a control unit 102 and an exposure switch 103 are not connected at all with an X-ray sensing apparatus which is a radiation sensing apparatus, and is handled independently of the X-ray sensing apparatus. The exposure switch 103 is a switch for starting the X-ray irradiation apparatus.

In the present embodiment, the radiation sensing apparatus can detect a start and an end of X-ray irradiation using a non-destructive read-out output of the radiation sensing apparatus without being synchronized with the X-ray irradiation apparatus by the direct connection with the X-ray irradiation apparatus. In FIG. 1, an X-ray sensing panel 105 is a sensing panel capable of reading out by non-destructively. The X-ray sensing panel 105 is composed of a plurality of photoelectric conversion elements arranged in two dimensions and a drive circuit of the elements. The circuit configuration of the X-ray sensing panel 105 and operations thereof will be described later in detail. The X-ray sensing panel 105 includes a waiting mode, a signal accumulation mode and a read-out mode as its drive mode.

A panel drive switch 107 is a switch connected with a drive control circuit 108 and a drive unit 106 to start the X-ray sensing panel 105 in the waiting mode. The drive control circuit 108 controls the drive unit 106 to switch the drive mode of the X-ray sensing panel 105 on the basis of an output of a comparator 109. A one-frame delay memory 120 stores image data of the preceding frame, and a differencing device 121 performs the subtraction processing of the image data of the preceding frame and the image data of the current frame to input the subtraction result into the non-inverting terminal (+) of the comparator 109. A reference value generation circuit 110 is a circuit for generating a reference value (REF value), and inputs the reference value into an inverting terminal (−). In the reference value generation circuit 110, the reference value is previously determined according to an image corresponding to a start and an end of X-ray irradiation. A start and a stop of irradiation of a radiation can be detected by performing the subtraction processing of the image data of the preceding frame and the image data of the current frame and by comparing the subtraction result with the reference value (REF value) in the comparator 109. The drive mode of the X-ray sensing panel 105 is switched on the basis of the detection result.

Here, in the present embodiment, as means for detecting a start and a stop of irradiation of a radiation from the X-ray source 101 on the basis of a signal obtained by the non-destructive read-out from the X-ray sensing panel 105 at the time of exposure, the means composed of the one-frame delay memory 120, the differencing device 121, the reference value generation circuit 110 and the comparator 109 is shown. However, any other configuration may be adopted as long as the configuration can perform the evaluation of variations of a non-destructive readout signal by comparing the non-destructive read-out signal with a prescribed reference value.

A reference numeral 111 designates an analogue-digital (A/D) converter performing the A/D conversion of a signal from the X-ray sensing panel 105 to output the converted signal to the one-frame delay memory 120 and an image processing circuit 112. The image processing circuit 112 processes an image signal from the A/D converter 111 to output the processed image signal to a monitor 113 for displaying a sensed image and a recording medium (memory) 114 for storing sensed image data.

Incidentally, a fluorescent substance for converting an X-ray to light such as visible rays is omitted in FIG. 1.

Figure 2:
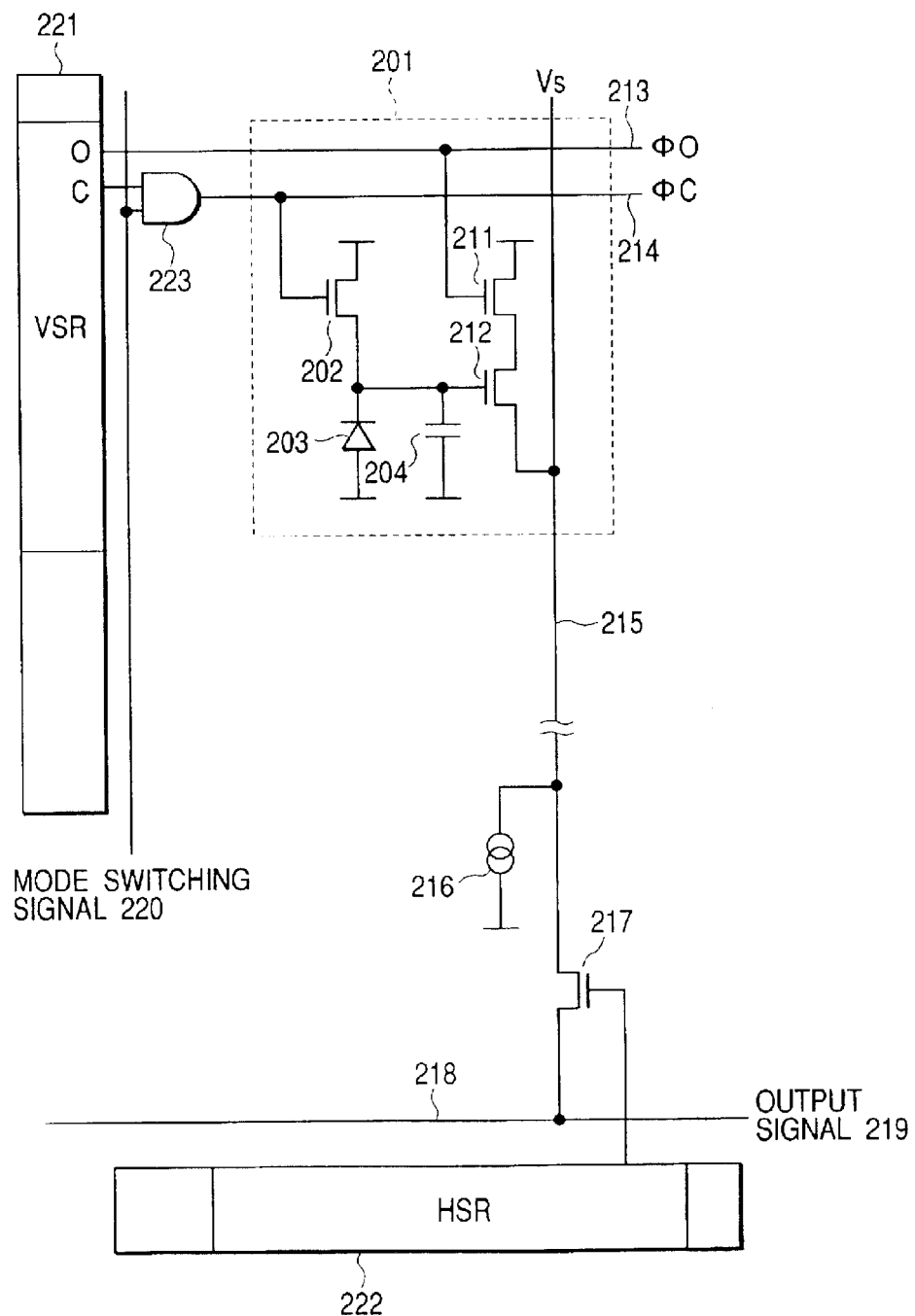
FIG. 2 is a circuit diagram showing the circuit of a part of the X-ray sensing panel of the embodiment of FIG. 1.

FIG. 2 is a circuit diagram showing a circuit of the X-ray sensing panel 105. Incidentally, FIG. 2 shows a part of the circuit of the X-ray sensing panel 105. In FIG. 2, a reference numeral 221 denotes a vertical shift register; a reference numeral 222 denotes a horizontal shift register; a reference numeral 223 denotes an AND gate; and a reference numeral 201 denotes a pixel unit. Moreover, a reference numeral 216 denotes a constant current source, and a reference numeral 217 denotes a metal oxide semiconductor (MOS) transistor for horizontal switching. A signal for instructing the drive mode, i.e. a mode switching signal 220 instructing either of the waiting mode and the signal accumulation mode, is input into the AND gate 223 from the drive control circuit 108 in FIG. 1. Moreover, a reference numeral 215 denotes a vertical read-out line through which a signal is read out from the pixel unit 201, and a reference numeral 218 denotes a horizontal read-out line through which signal outputs are read out from each of the vertical read-out lines 215 in order. Moreover, a reference numeral 213 denotes a row output selection line connected with the gate of a transistor for vertical output switching 211, and a reference numeral 214 denotes a reset line connected with the gate of a MOS transistor for resetting 202.

The pixel unit 201 is composed of the MOS transistor for resetting 202, the MOS transistor for vertical output switching 211, a MOS transistor for read-out 212, a photoelectric conversion element 203 and a capacitor 204. The pixel unit 201 constitutes together with the constant current circuit 216 an amplifier having a voltage amplification factor being one time. At the time of read-out, the electric charge of the photoelectric conversion element 203 does not move, and consequently it is possible to perform a read-out operation independently of resetting.

The photoelectric conversion element 203 and the capacitor 204 are connected with the gate terminal of the MOS transistor for read-out 212 in the pixel unit 201 to form a source follower circuit together with the constant current source 216. Consequently, the information of the signal charges of the photoelectric conversion element 203 can be read out on the vertical read-out line 215 without any current flowing through the gate terminal of the MOS transistor for read-out 212, and the signal charges of the photoelectric conversion element 203 do not move at the time of read-out. Consequently, it is possible to perform, the non-destructive read-out. Incidentally, a resistor can be used instead of the constant current source 216. However, it is desirable to use the constant current source 216 to improve the precision of the source follower circuit.

In the present embodiment, the photoelectric conversion element 203 is connected with the gate terminal of the MOS transistor for read-out 212. However, the present invention is not limited to such a configuration. It is possible to perform the non-destructive read-out by connecting the photoelectric conversion element 203 with the control terminal of an element or a circuit which performs an amplification operation. This is because any electric current does not flow through the control terminal and no electric charges move. And further, even if some electric charges flow, only an electric current far smaller than an electric current or electric charges which are necessary for an output flows through the control terminal on the basis of the principle of amplification. The far smaller electric current is negligible. For example, the non-destructive read-out can be also performed by connecting the photoelectric conversion element 203 with a base terminal of a bipolar transistor for read-out.

FIGS. 3A to 3J are timing charts showing the operations in the waiting mode (performing a reset after non-destructive read-out), and FIGS. 4A to 4J are timing charts showing the operations in the signal accumulation mode (performing non-destructive read-out). The difference between the waiting mode and the signal accumulation mode is whether a reset is performed after read-out or not. As it will be described later, in the waiting mode, non-destructive read-out in a frame is performed first, and if irradiation of an X-ray is not detected, a reset is performed. Consequently, unless any X-ray is detected (as long as the radiation sensing apparatus is in the waiting mode), the signals in pixels are destroyed (discharged). When irradiation of an X-ray is detected, the reset of the frame is stopped, and the radiation sensing apparatus immediately enters into the signal accumulation mode. Read-out during the signal accumulation mode is continued as the non-destructive read-out. That is, signals are accumulated in pixels, and at the same time non-destructive read-out is performed without destroying the signals. When a stop of the X-ray irradiation is detected by the non-destructive read-out, the radiation sensing apparatus immediately enters into the read-out mode, and uses the read-out data of the frame as image data. After that, a reset is performed, and then the next operation (of the waiting mode) is performed. Consequently, the read-out in the read-out mode is destructive read-out.

Figure 3:
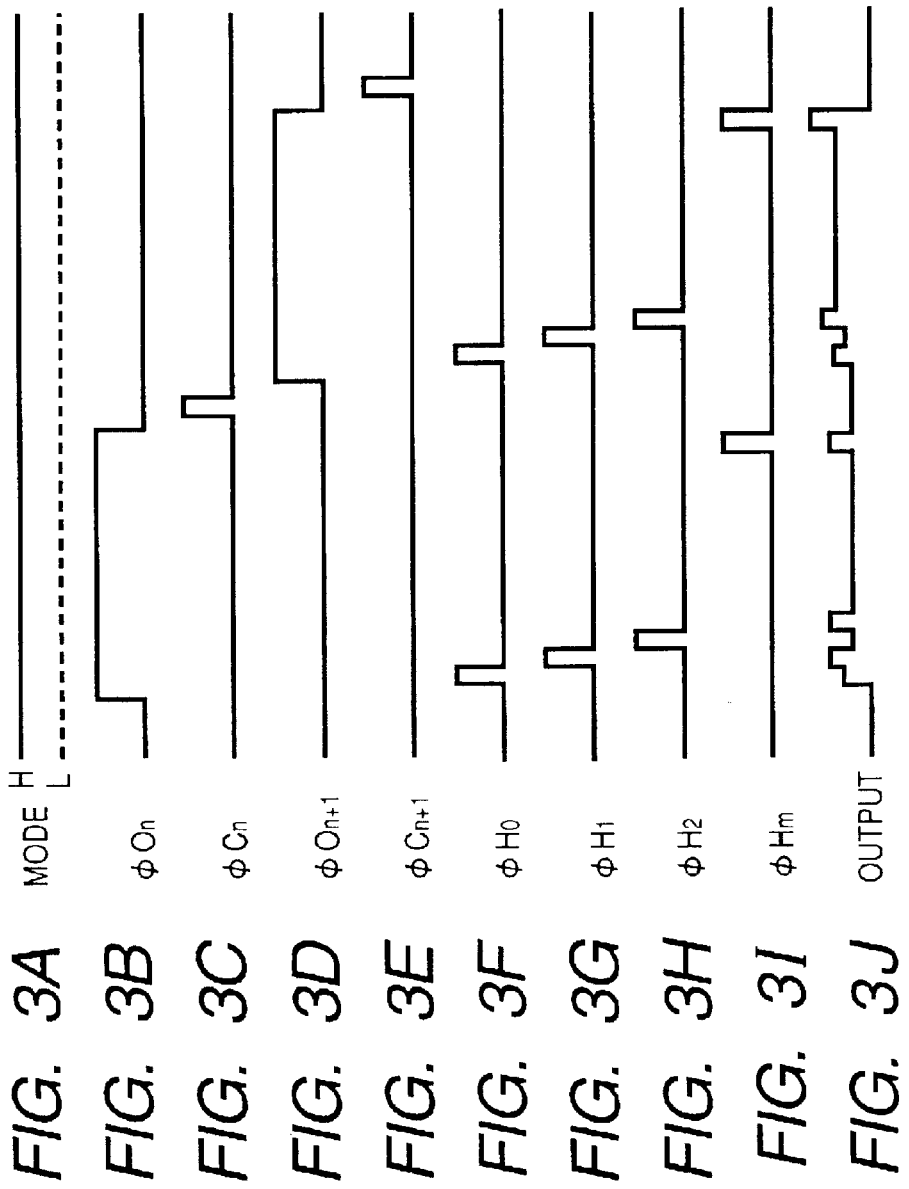
FIGS. 3A, 3B, 3C, 3D, 3E, 3F, 3G, 3H, 3I and 3J are timing charts showing the operations in a waiting mode.

First, FIGS. 3A to 3J are referred while the operation in the waiting mode is explained. As shown in FIG. 3A, in the waiting mode, a high level mode switching signal is supplied to the AND gate 223 in the X-ray sensing panel 105 from the drive control unit 106. In this state, as shown in FIG. 3B, when a signal $\phi O_n$ (high level) is output from the vertical shift register 221, the MOS transistors for vertical output switching 211 are turned on.

At this time, because the circuit including the MOS transistor for read-out 212 constitutes a source follower and then is an amplification circuit having a voltage amplification factor being about one time, the signal charge of the photoelectric conversion element 203 is read out as it is on the vertical read-out lines 215. Moreover, although it is omitted in FIG. 2, a plurality of pixel units are disposed in a row direction, and the signal charge of each pixel unit of one line in the row direction is read out on the vertical read-out line 215. Moreover, although it is omitted in FIG. 2, a plurality of pixel units are disposed in a column direction, and a plurality of pixel units 201 are disposed in an matrix form in row directions and column directions.

Next, as shown in FIG. 3F, a signal $\phi H_0$ is output from the horizontal shift register 222, and then the MOS transistor for horizontal output switching 217 is turned on. Thereby, as shown in FIG. 3J, an output on the vertical read-out line 215 is read out on the horizontal read-out line 218. Successively, as shown in FIGS. 3G to 3I, signals $\phi H_1, \phi H_2, \ldots, \phi H_m$ are output from the horizontal shift register 222 in order, and, as shown in FIG. 3J, the signal charges of one line in a row direction are read out on the horizontal read-out line 218 in order. After the operations described above have ended, the read-out of a first line in the row direction is completed.

Next, as shown in FIG. 3C, a signal $\phi C_n$ is output to the AND gate 223 from the vertical shift register 221, and then the MOS transistor for resetting 202 is turned on. Thereby, the signal charge of the photoelectric conversion element 203 is initialized (reset). Moreover, the signal charges of the other pixel units of the one line in the row direction are similarly reset, and electric charges are newly accumulated in the photoelectric conversion elements 203 during the next accumulation period.

Next, as shown in FIG. 3D, a signal $\phi O_{n+1}$ is output from the vertical shift register 221 to the pixels (not shown) in a second row, and the MOS transistors for vertical output switching 221 are turned on. Thereby, the signal charges of the photoelectric conversion elements 203 of the second line are read out onto the vertical read-out line 215. Moreover, as shown in FIGS. 3F to 3I, the signals $\phi H_1, \phi H_2, \ldots, \phi H_m$ are output from the horizontal shift register 222 in order, and, as shown in FIG. 3J, the signal charges on the vertical read-out lines 215 are read out onto the horizontal read-out line 218 in order.

After that, as shown in FIG. 3E, a signal $\phi C_{n+1}$ is output to the AND gate 223 from the vertical shift register 221, and the photoelectric conversion elements 203 in the pixel units in the second row are reset. Then, the signal charges of the pixel units of a third line, a fourth line and so on are similarly read out. When the signal charges on the last line have been read out, the read-out of all of the pixel units of the X-ray sensing panel 105 is completed.

Figure 4:
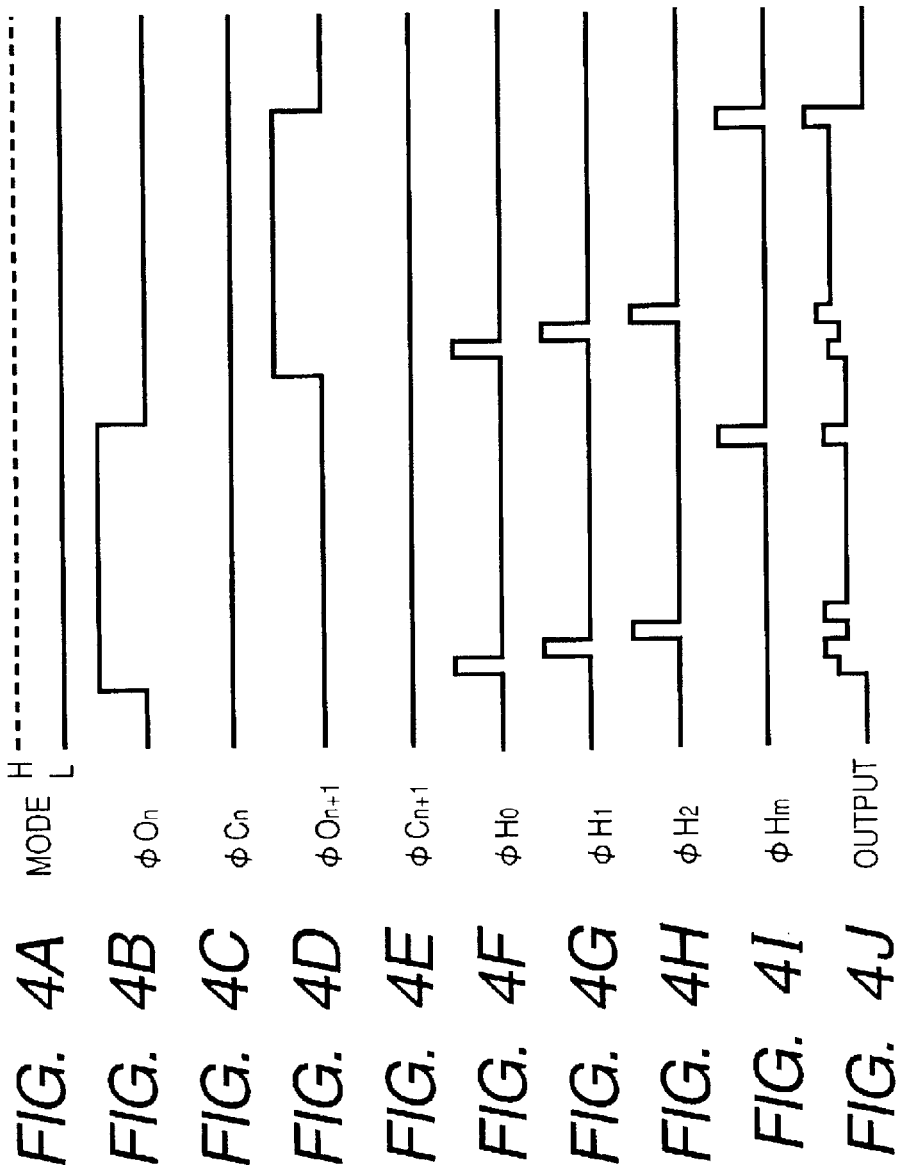
FIGS. 4A, 4B, 4C, 4D, 4E, 4F, 4G, 4H, 4I and 4J are timing charts showing the operations in a signal accumulation mode.

Next, FIGS. 4A to 4J are referred while the operations in the signal accumulation mode after the X-ray irradiation is detected with the method which will be described later are described. Although signal charges of the photoelectric conversion elements 203 are reset after the signal charges have been read out in the waiting mode as described above, the signal accumulation mode is different from the operation in the waiting mode in that the signal accumulation mode does not reset signal charges of the photoelectric conversion elements 203 after the read out of the signal charges. When the radiation sensing apparatus enters into the signal accumulation mode, the apparatus performs non-destructive read-out. Consequently, as shown in FIG. 4A, in this case, a mode switching signal being a low is supplied to the X-ray sensing panel 105 from the drive control unit 106. Consequently the AND gate 223 is kept to be in its closed state.

In this state, as shown in FIG. 4B, the signal $\phi O_n$ is output from the vertical shift register 221, and then the MOS transistor for vertical output switching 211 is turned on. Thereby, the signal charge of the photoelectric conversion element 203 is read out on the vertical read-out line 215 through the MOS transistor for read-out 212. Next, as shown in FIG. 4F, the signal $\phi H_0$ is output from the horizontal shift register 222, and then the MOS transistor for horizontal output switching 217 is turned on. Thereby, as shown in FIG. 4J, an output on the vertical read-out line 215 is read out on the horizontal read-out line 218. Successively, as shown in FIGS. 4G to 4I, the signals $\phi H_1, \phi H_2, \ldots, \phi H_m$ are output from the horizontal shift register 222 in order, and, as shown in FIG. 4J, the signal charges of one line in a row direction are read out onto the horizontal read-out line 218 in order. After the operations described above have ended, the read-out of one line in the row direction is completed.

Next, as shown in FIG. 4D, the signal $\Phi O_{n+1}$ is output from the vertical shift register 221 to the pixel units (not shown) in the second row, and then the MOS transistors for vertical output switching 221 are turned on. Thereby, the signal charges of the photoelectric conversion elements 203 of the second line are read out onto vertical read-out line 215. Moreover, as shown in FIGS. 4F to 4I, the signals $\phi H_1$ to $\phi H_m$ are output from the horizontal shift register 222 in order, and, as shown in FIG. 4J, the signal charges on the vertical read-out lines 215 are read out to the horizontal read-out line 218 in order.

Subsequently, the signal charges of the pixel units of the third line, the fourth line and so on are similarly read out. When the signal charges on the last line have been read out, the read-out of all of the pixel units of the X-ray sensing panel 105 is completed.

As described above, in the signal accumulation mode, non-destructive read-out is performed. After the read-out of the signal charges in the pixel units, the next accumulation is started without resetting the signal charges of the photoelectric conversion elements 203, and the accumulation of signals is continued. That is, the quantities of electric charges do not change before and after read-out of pixel units. The photoelectric conversion elements 203 are not influenced by the operation of read-out. In the present embodiment, a start and a stop of X-ray irradiation are detected by the non-destructive read-out as it will be described later in detail. Then, the control of the radiation sensing apparatus is performed without connecting it with the X-ray irradiation apparatus directly.

FIGS. 5A to 5F are timing charts showing the operations of the X-ray sensing apparatus of the present embodiment. In the following, FIGS. 1, 2, 3A to 3J, 4A to 4J, and 5A to 5F are referred while concrete operations of the present embodiment are described.

First, when the panel drive switch 107 is turned on, a drive starting signal (not shown) is transmitted to the panel drive circuit (drive unit) 106, and then the driving of the X-ray sensing panel 105 is started.

Figure 5:
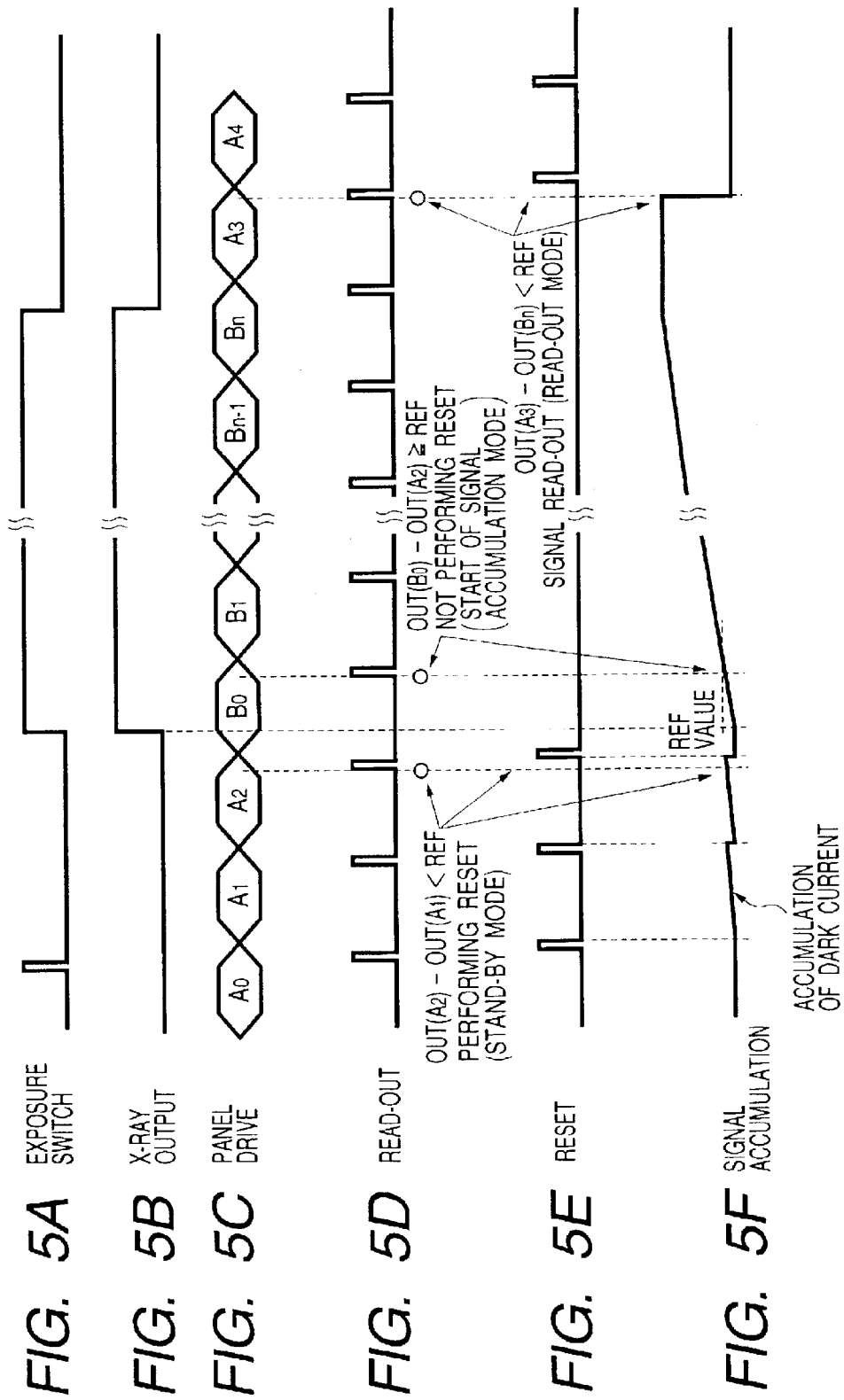
FIGS. 5A, 5B, 5C, 5D, 5E and 5F are explanatory views for illustrating the operations of detecting a start and a stop of X-ray irradiation in conformity with the non-destructive read-out of the embodiment of FIG. 1.

After the X-ray sensing panel 105 is driven, the exposure switch 103 is depressed, and the X-ray irradiation apparatus is operated. The X-ray drive circuit (control unit) 102 drives the X-ray source 101, and thereby an X-ray is irradiated from the X-ray source 101 as shown in FIG. 5B. The X-ray permeates the subject 104 and is converted into visible rays by a fluorescent substance (not shown). And then, the converted visible rays are input into the X-ray sensing panel 105.

FIG. 5A shows an exposure starting signal from the exposure switch 103. When the first stage switch of the exposure switch 103 is turned on, as shown in FIG. 5A, a signal instructing exposure is supplied to the X-ray drive circuit (control unit) 102.

After a predetermined period of time, when the second stage switch of the exposure switch 103 is depressed, the exposure of an X-ray is started. In case of a rotation anode type X-ray tube, the predetermined period of time is a period of time necessary for starting the rotation of an X-ray tube, reaching a predetermined number of rotations, and further making the temperature of the electron source of the X-ray tube constant.

FIG. 5C shows an operation of the X-ray sensing panel 105. Reference numerals $A_0$, $A_1$, $A_2$, $A_4$, . . . denote frame operations in the waiting mode. Reference numerals $B_0$ to $B_n$ denote frame operations in the signal accumulation mode (non-destructive read-out). A reference numeral $A_3$ denotes a frame operation in the read-out mode. Moreover, when the drive control circuit 108 receives a start signal from the panel drive switch 107, the drive control circuit 108 starts to drive the X-ray sensing panel 105 in the waiting mode by supplying a high level signal instructing the waiting mode to the AND gate 223 of the X-ray sensing panel 105 through the drive unit 106. In this case, because resetting is performed after the read-out of each frame, the read-out operations are destructive read-out.

Consequently, as shown in FIG. 5C, a first frame of the read-out of the X-ray sensing panel 105 starts a frame operation $A_0$ in the waiting mode, and the read-out of the X-ray sensing panel 105 continues the waiting mode until the panel 105 detects an X-ray. A second frame and the subsequent frames are read out in frame operations $A_1$ and $A_2$. At a time of the completion of each frame read-out, the differencing device 121 calculates the difference between the read-out signal charge and the signal charge of the preceding frame stored in the one-frame delay memory 120, and calculates the quantity of signal accumulation of one frame of each pixel. That is, the output value of the A/D converter 111 read in the frame operation $A_1$ is subtracted from the output value of the A/D converter 111 read in the frame operation $A_2$, and the calculation of $OUT(A_2)-OUT(A_1)$ is performed. Thereby, a signal accumulation quantity is calculated. At this point of time, resetting of the frame is not performed, and the frame operation $A_1$ is performed in the non-destructive read-out. The calculation of the signal accumulation quantity is performed to all of the pixels. The reference value generation circuit 110 generates a REF value corresponding to a 'signal generated by a dark current accumulated in a pixel during one frame.

The comparator 109 compares an output value of the differencing device 121 (signal accumulation quantity) with the REF value. As shown in FIG. 5D, if the output value of the differencing device 121 $OUT(A_2)-OUT(A_1)$ is smaller than the REF value ($OUT(A_2)-OUT(A_1)<REF$ value), the radiation sensing apparatus judges that no X-ray irradiation is performed, and performs a reset of the radiation sensing apparatus immediately (the read-out becomes destructive read-out at this point of time) to enter the next frame operation. Such processing is performed at read-out in every frame, and the radiation sensing device continues the waiting mode until it detects the irradiation of an X-ray.

As shown in FIG. 5F, when the output value of the differencing device 121 becomes equal to the REF value or more ($OUT(B_0)-OUT(A_2) \geq REF$ value), the radiation sensing apparatus decides that the irradiation of an X-ray is begun, and stops any reset after that to enter the signal accumulation mode. That is, in this case, as shown in FIG. 4A, a mode switching signal having the low level is supplied to the X-ray panel 105 from the drive unit 106, and the AND gate 223 is kept to be closed to stop resetting.

Because the frame operation $B_0$ is not reset, the frame operation $B_0$ is the non-destructive read-out, and the signal due to the X-ray irradiation accumulated in the frame is used as an image signal as it is. In the conventional X-ray irradiation detection using an image sensor of the destructive read-out, the signal in the frame in which an X-ray is detected first is discharged, and the signals of the next and succeeding frames are used as image signals. Consequently the conventional X-ray irradiation detection renders a part of the X-ray useless, but the X-ray irradiation detection according to the present invention does not render the X-ray useless.

The X-ray is irradiated for a previously set period of time. The above-mentioned non-destructive read-out operation is repeated during the period of time. If the output value of the differencing device 121 is equal to the REF value or more, the signal accumulation mode is continued.

When the X-ray irradiation ends, the signal accumulation quantity does not increase except that due to a dark current. In this case, the output value of the differencing device 121 becomes smaller than the REF value ($OUT(A_3)-OUT(B_n)$ <REF value). At this time, the radiation sensing apparatus judges that the X-ray irradiation is ended, and enters into the read-out mode.

As shown in FIG. 5D, the image signal is read out from the X-ray sensing panel 105 in the frame operation $A_3$. After the read-out of the image signal, resetting is performed and the drive of the X-ray sensing panel 105 is stopped. The image processing circuit 112 performs the operation of $OUT(A_3)-OUT(A_2)$ by the use of this read image signal and the image signal in the frame operation $A_2$ being before the start of the X-ray irradiation, and outputs an obtained result. Needless to say, the operation is performed to all of the pixels. Thereby, an output corrected by a predetermined pattern noise (FPN) correction can be obtained, and the image processing circuit 112 displays the sensed image on the monitor 113, and further the image processing circuit 112 stores the image in the recording medium 114 as image data.

Although the drive of the X-ray sensing panel 105 is ended after the read-out of the image signal in the frame operation $A_3$, the operations of obtaining dark currents and the FPN signal may be performed for the same period of time as that of the signal accumulation of the X-ray image, and the image signal may be treated as FPN data.

Incidentally, although all of the pixels are read out at the time of the read-out for detecting the start and the end of the X-ray irradiation, partial read-out (read-out performed by thinning-out (jumping) pixel columns and/or pixel rows), pixel addition read-out, random access read-out only to effective reference positions may be performed. The detection sensitivity of changes of the X-ray can be increased by providing addition means in a pixel to read out signals while performing pixel addition during the waiting mode and the signal accumulation mode. Because the accumulated image signal is generally required to have the maximum resolution, the read-out of all of the pixels is a standard. However, it is possible to read out image signals in the pixel addition mode during image signal read-out for some uses. Because it is enough for the non-destructive read-out during a wait of X-ray irradiation (waiting mode) or during a period for the detection of the end of X-ray irradiation (during signal accumulation mode) to detect an X-ray, it is unnecessary to read all of the pixels. The read-out of actual sensing after the irradiation of the X-ray has been begun (destructive read-out in the read-out mode), is considerable to read out, for example, all of the pixels at the maximum resolution, or to read out every four pixels or the like to be added by decreasing the resolution. In this case, the read-out method in which the number of pixels to be added in the non-destructive read-out and the number of pixels to be added in the sensed image read-out (including the case where no pixels are added) differ from each other may be adopted. Moreover, if random access read-out is performed, because electric charges do not change before and after the read-out, the next frame is not influenced at all. This is a feature of the non-destructive read-out.

When the read-out at every line is performed during the detection of an X-ray as in the present embodiment, the X-ray is irradiated during the read-out, and the signal quantity of each line varies. That is, the later the read-out is performed, the. more the accumulation quantity becomes. Consequently, it is possible to provide means for optimizing a part of a frame to be used for performing the detection of X-ray irradiation more precisely. Moreover, as it will be shown in a second embodiment, by providing an electric shutter function to the pixel units, the radiation sensing apparatus can be operated by batch exposure. By adopting such a method, the signal accumulation of all of the pixels can be performed for a predetermined period of time at the same timing.

In the present embodiment, the non-destructive read-out is performed one time per frame during the waiting mode. The number of times, timing and the like of the pieces of non-destructive read-out in a frame can be optimized in conformity with algorithm of X-ray detection (for example, in case of detecting an X-ray at a higher speed and higher sensitivity by setting the speed of non-destructive read-out higher than that of a frame, and by adopting the method of pixel addition read-out).

Incidentally, although a fluorescent substance is used for converting an X-ray to the light such as visible rays in the present embodiment, the conversion may be performed by the use of a general scintillator, i.e. a waveform conversion body. Moreover, even if the fluorescent body is not used, a photoelectric conversion element which detects a radiation directly by itself to generate electric charges may be adopted.

Moreover, although the descriptions are given to the case where an X-ray is used in the present embodiment, radiations such as an α ray, a β ray and a γ ray can be used.

Second Embodiment

In the present embodiment, a start and a stop of X-ray irradiation are detected by non-destructive read-out, and the optimum exposure quantity is detected by non-destructive read-out. And, when the optimum exposure quantity is detected, signal read-out is performed before the stop of the X-ray irradiation. The read-out is performed by the use of the electric shutter function and by the batch exposure read-out.

Figure 6:
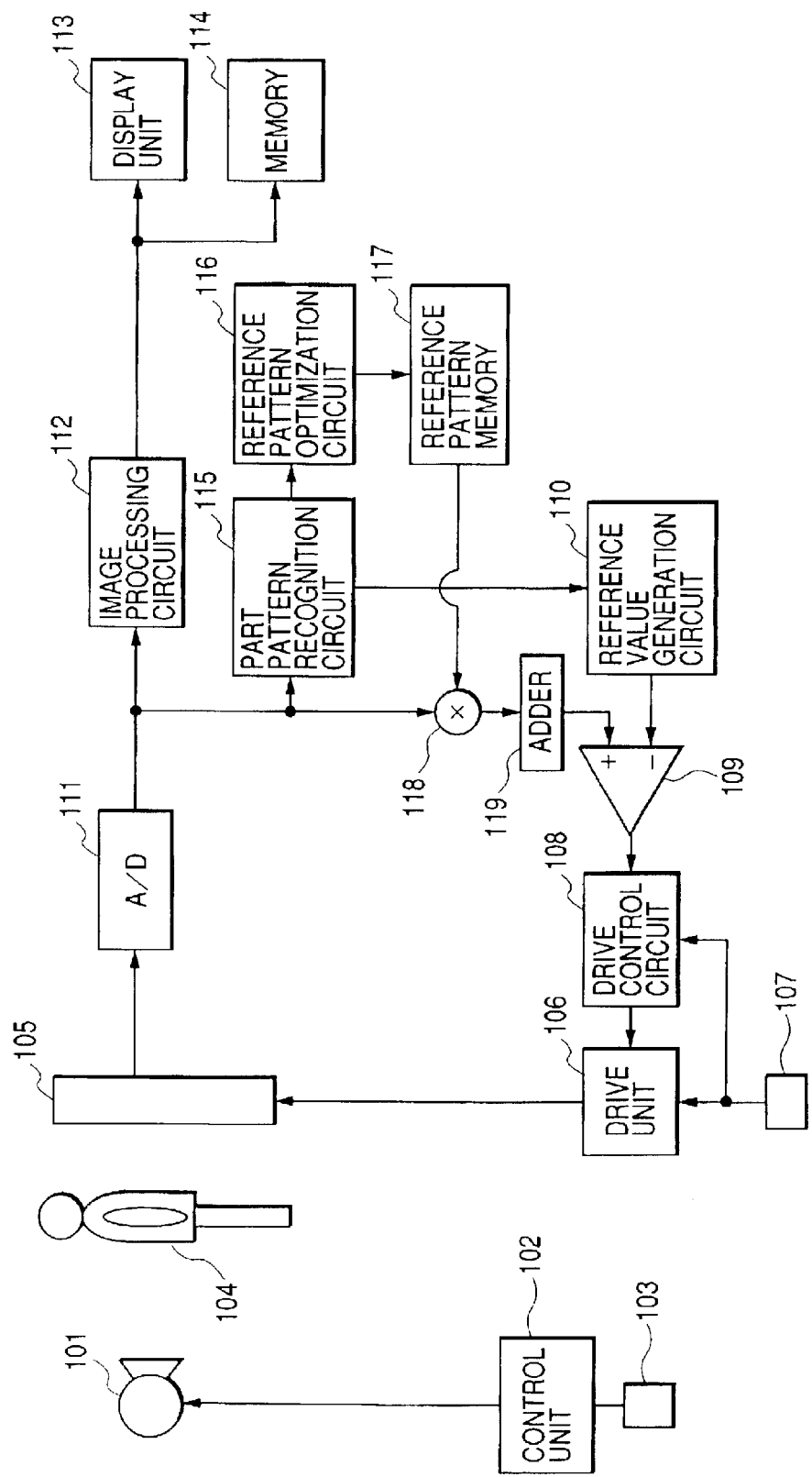
FIG. 6 is a block diagram showing the configuration of a second embodiment of the present invention.

FIG. 6 is a block diagram showing the configuration of the second embodiment of the radiation sensing apparatus of the present invention. Incidentally, the same units of the apparatus of FIG. 6 as those of the apparatus of FIG. 1 are designated by the same reference numerals, and their descriptions are omitted.

First, it is supposed that still images of, for example, a lung, a stomach, a breast and the like of a human being are sensed in the present embodiment. By the use of outputs of non-destructive read-out, the detection of a start and an end of X-ray irradiation and the evaluation of the optimum exposure are performed. In FIG. 6, because the detection units of the start and the end of the X-ray irradiation are the same as those of the embodiment 1, the units are omitted to be shown, and a system for performing the evaluation of the optimum exposure is shown. As means for detecting the start and the end of the irradiation of a radiation from the X-ray source 101 on the basis of a signal obtained by non-destructive read-out from the X-ray sensing panel 105, the one-frame delay memory 120, the differencing device 121, the reference value generation circuit 110 and the comparator 109 are separately provided, and an output of the comparator 109 is input into the drive control circuit 108 of FIG. 6. The circuit configuration and the operation of the X-ray sensing panel 105 will be described later in detail.

The drive control circuit 108 is a circuit for switching the drive mode of the X-ray sensing panel 105 between the waiting mode and the signal accumulation mode. A part pattern recognition circuit 115 is a circuit performing the pattern recognition of an image sensed by the X-ray sensing panel 105 on the basis of the output value of the A/D converter 111. That is, the part pattern recognition circuit 115 performs the pattern recognition to discriminate what part of an image an image sensed on the basis of the output value of the A/D converter 111 is (for example, a lung, a stomach, a breast, a hand, a leg and the like). As a result, the position and the size of the sensed image are detected.

A reference pattern optimization circuit 116 is a circuit for determining the optimum value of a reference pattern at every pixel on the basis of a pattern recognition result of the part pattern recognition circuit 115. That is, the reference pattern optimization circuit 116 judges which position of the image subjected to its pattern recognition should be observed preponderantly on the basis of the recognition result of the pattern recognition, and stores the judged numerical values in every pixel of a reference pattern memory 117 to make the reference pattern memory 117. In the present embodiment, weighting is performed as three steps of 0, 1 and 2 in the present embodiment to simplify the description thereof. In this case, a numeral 0 indicates not being any object (a position unnecessary to be seen); a numeral 2 indicates a position to be seen preponderantly; and a numeral 1 indicates a position to make an image better totally. Incidentally, although the weighting is made as the three steps to simplify the description in the present embodiment, it is needless to say that it is possible to obtain an image having further better image quality by performing the weighting of further multi-steps.

The reference numeral generation circuit 110 is a circuit for generating a reference value (REF value) on the basis of a pattern recognition result of the part pattern recognition circuit 115. That is, in the reference value generation circuit 110, the REF value has previously been determined according to an image. The reference value generation circuit is configured to set the REF value large, if the result of pattern recognition is, e.g. a lung, because the lung requires a high signal to noise (S/N) ratio, and is configured to set the REF value to be small, if the result is a stomach.

Incidentally, in FIG. 6, the reference pattern memory 117 has a storage area composed of 8×8 pixels, and stores a numerical value weighted by any one of 0, 1 and 2 in every pixel. This configuration is one supposed to simplify illustration. Actually, the X-ray sensing panel 105 includes further many pixels, and the storage area of the reference pattern memory 117 includes further many memory cells correspondingly to those of the X-ray sensing panel 105.

A multiplier 118 is a circuit for multiplying the numerical value of each pixel in the reference pattern memory 117 by the output value of A/C conversion of each pixel of the X-ray sensing panel 105. The multiplier 118 performs the multiplications of the values of corresponding pixels of both of the reference pattern memory 117 and the X-ray sensing panel 105, and outputs the calculation results to an adder 119. The output values of the adder 119 are the results of the weighted additions of the output values of the A/D conversion and the numerical values of the reference pattern memory 117.

The comparator 109 compares the output values of the adder 119 with the REF value of the reference value generation circuit 110. When an output value of the adder 119 becomes equal to the REF value or more during X-ray irradiation (namely before the detection of the X-ray irradiation by the non-destructive read-out), the comparator 109 outputs a signal instructing the read-out mode to the panel drive circuit to read out image signals.

Here, in the present embodiment, the means composed of the part pattern recognition circuit 115, the reference pattern optimization circuit 116, the reference pattern memory 117, the multiplier 118, the adder 119, the reference value generation circuit 110 and the comparator 109 is shown as the evaluation means for evaluating the radiation exposure quantity from the radiation source on the basis of the signals read out from the X-ray sensing panel 105 by the non-destructive read-out at the time of exposure. However, the configuration composed of only the comparator comparing a prescribed reference value with the signals read out non-destructively to evaluate the exposure quantity as the optimum exposure when the signal read out non-destructively is a predetermined value or more may be adopted.

Incidentally, the exposure switch 103, the image processing circuit 112, the monitor 113 and the recording medium 114 are the same as those shown in FIG. 1. Moreover, in FIG. 6, a fluorescent substance for converting X-rays into light such as visible rays is omitted.

Figure 7:
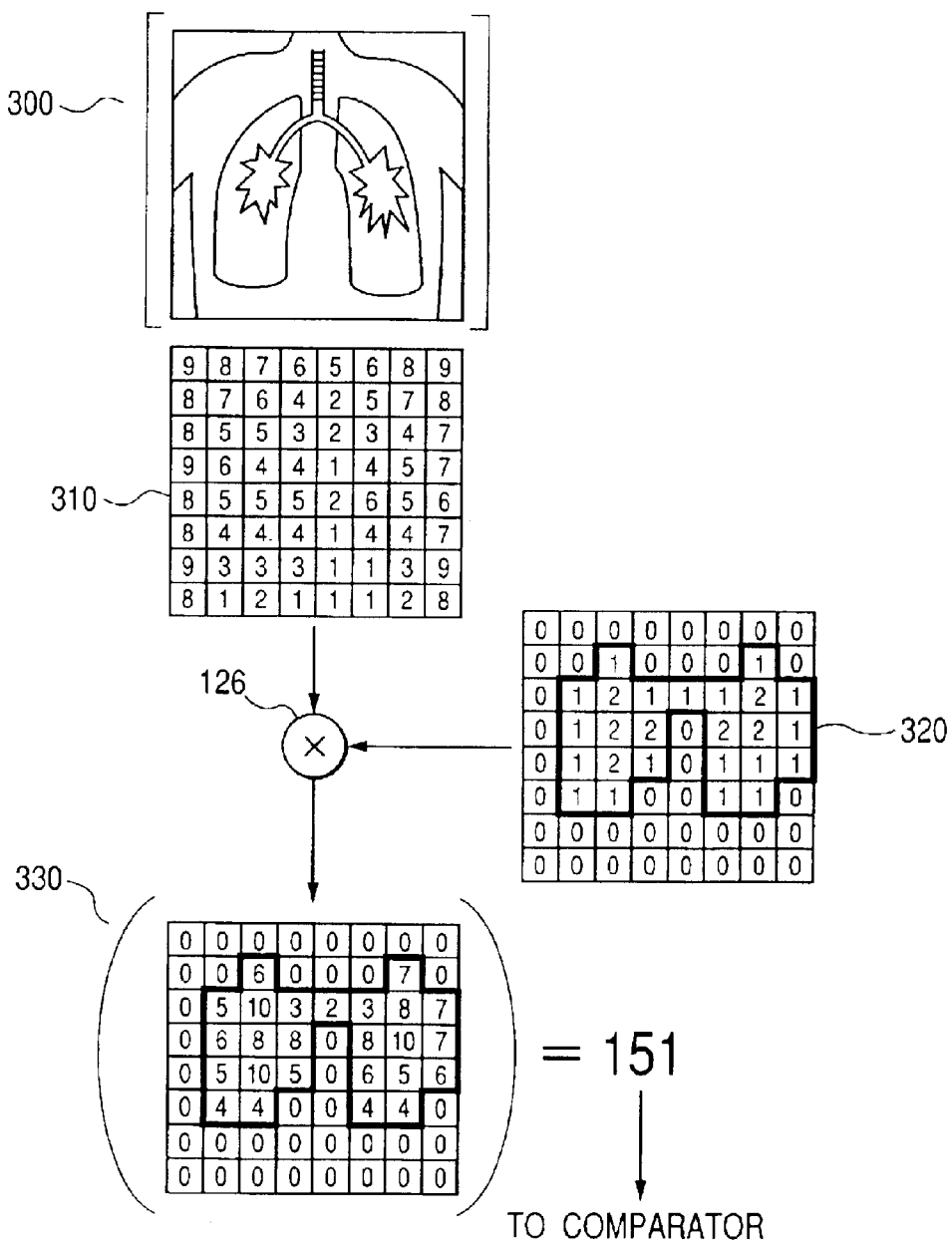
FIG. 7 is an explanatory view for illustrating an operation of evaluating the optimum exposure quantity in conformity with the non-destructive read-out of the embodiment of FIG. 6.

FIG. 7 is a drawing for illustrating the operations of the present embodiment for detecting exposure quantities. A reference numeral 300 denotes an image on the X-ray sensing panel 105, and a reference numeral 310 denotes output values of the A/D converter 110 at every pixel of the X-ray sensing panel 105. Moreover, a reference numeral 320 denotes numeral values at every pixel in the reference pattern memory 117, and a reference numeral 330 denotes numerical values at every pixel of the adder 119. Incidentally, also in FIG. 7, it is supposed that the X-ray sensing panel 105 has 8×8 pixels to simplify the drawing.

The multiplier 118 performs the multiplications of the output values 310 of the A/D converter 110 at every pixel of the X-ray sensing panel 105 by the numerical values 320 of the reference pattern memory 117. The outputs of the multiplier 118 are output to the adder 119, and the adder 119 performs the additions of the numerical values of all of the pixels. In this case, an output value of the adder 119 (151 in the example of FIG. 7) is output as a numerical value indicating the present exposure quantity to the comparator 109. When the added value exceeds the REF value, the comparator 109 output a signal instructing a read-out mode to the panel drive circuit to read out image signals.

Figure 8:
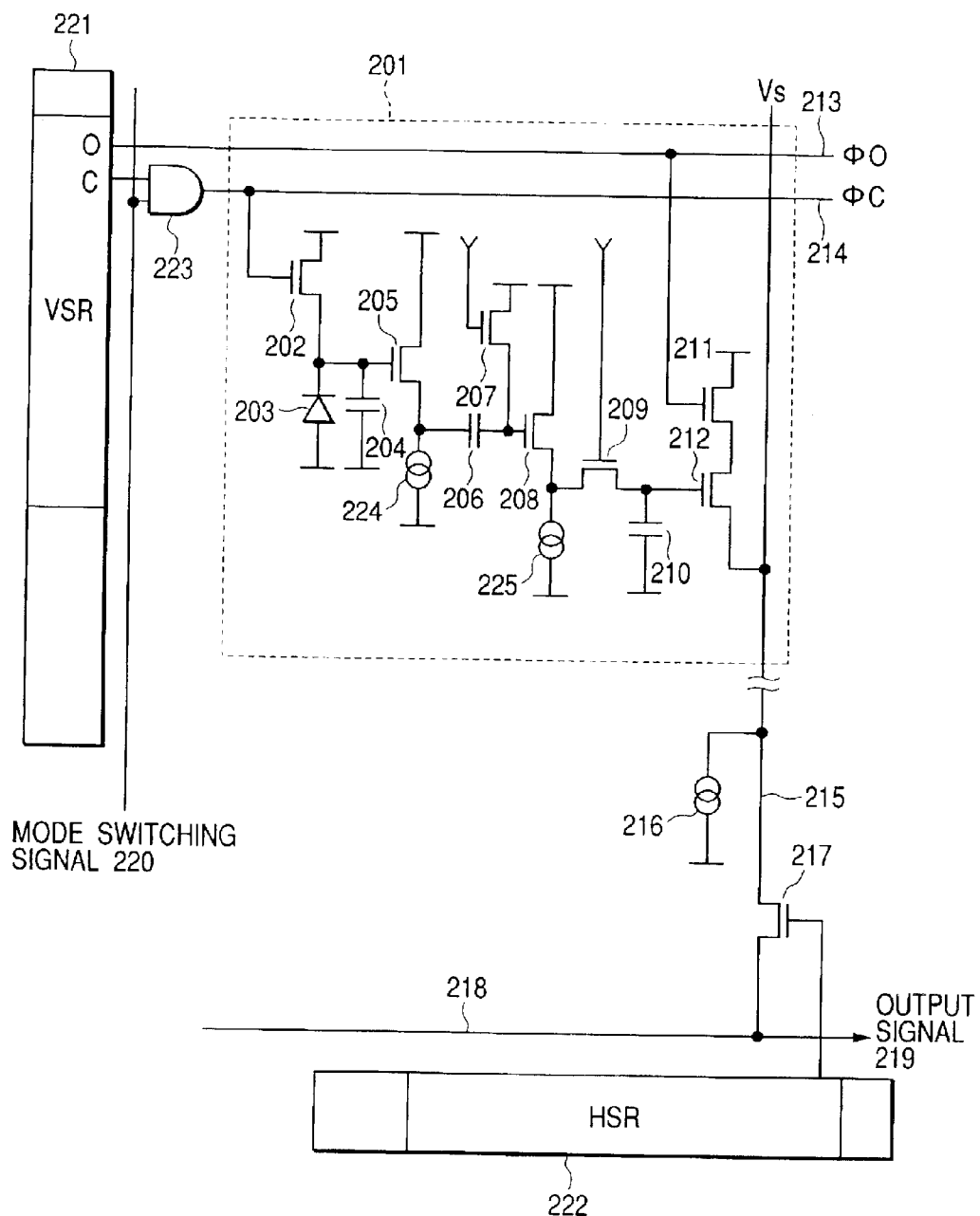
FIG. 8 is a circuit diagram showing the circuit of a part of the X-ray sensing panel of the embodiment of FIG. 6.

FIG. 8 is a circuit diagram showing a circuit of the X-ray sensing panel 105. Incidentally, FIG. 8 shows a part of the circuit of the X-ray sensing panel 105. In FIG. 8, a reference numeral 221 denotes a vertical shift register; a reference numeral 222 denotes a horizontal shift register; a reference numeral 223 denotes an AND gate; and a reference numeral 201 denotes a pixel unit. Moreover, a reference numeral 216 denotes a constant current source, and a reference numeral 217 denotes a MOS transistor for horizontal switching. A signal for instructing the drive mode, i.e. a mode switching signal 220 instructing either of the waiting mode and the signal accumulation mode, is input into the AND gate 223 from the drive control circuit 108 in FIG. 6. Moreover, a reference numeral 215 denotes a vertical read-out line through which a signal is read out from the pixel unit 201, and a reference numeral 218 denotes a horizontal read-out line through which signal outputs are read out from each of the vertical read-out lines 215 in order. Moreover, a reference numeral 213 denotes a row output selection line connected with the gate of a transistor for vertical output switching 211, and a reference numeral 214 denotes a reset line connected with the gate of a MOS transistor for resetting 202.

The pixel unit 201 includes the MOS transistor for resetting 202, a photoelectric conversion element 203, a capacitor 204, and a first source follower amplifier 205, a constant current source 224 (constituting a first source follower circuit). The pixel unit 201 further includes a clamp circuit (composed of a clamp capacitor 206 and a clamp switch 207) for eliminating kTC noises of the photoelectric conversion element 203, and a sample and hold (S/H) circuit (composed of a sampling switch 209 and a sampling capacitor 210) as an electronic shutter for performing batch exposure. The pixel unit 201 includes a constant current source 225 and a second source follower amplifier 208 (constituting a second source follower circuit) between the clamp circuit and the sample and hold circuit (S/H circuit). A MOS transistor for read-out (a third source follower amplifier) 212 and the constant current source 216 in the pixel unit 201 constitutes a third source follower circuit together.

The amplifiers each constitute an amplifier having a voltage amplification factor being one time. At the time of read-out, signal charges do not move, and consequently it is possible to perform a read-out operation independently from resetting. The photoelectric conversion element 203 and the capacitor 204 are connected with, for example, the gate terminal of the MOS transistor 205 to form a source follower circuit together with the constant current source 224. Consequently, the information of the signal charges of the photoelectric conversion element 203 can be read out on the next stage without any current flowing through the gate terminal of the MOS transistor 205, and the signal charge of the photoelectric conversion element 203 does not move at the time of read-out. Consequently, it is possible to perform non-destructive read-out. This feature is true in the second and the third source follower circuits similarly. Incidentally, resistors can be used instead of the constant current sources 216, 224 and 225. However, it is desirable to use the constant current sources 216, 224 and 225 to improve the precision of the source follower circuits. Although the source follower circuits are constituted by means of MOS transistors 205, 208 and 212 in the present embodiment, the present invention is not limited to such configurations. Non-destructive read-out can be performed by connecting the output of the photoelectric conversion element 203 with a control terminal of a device or a circuit, both having an amplification function. This is because an electric current does not flow into the control terminal, which makes the electric charges not move, and that, even if the electric charges move, only the electric charges smaller by far than the electric current or the electric charges which are necessary for an output, flow into the control terminal on the basis of the principle of amplification. If the electric current is smaller by far, the electric current is negligible. Accordingly, it is possible to perform the non-destructive read-out by connecting the output of the photoelectric conversion element 203 with, for example, a base terminal of a bipolar transistor for read-out.

The operations in the waiting mode and the signal accumulation mode which are executed in the circuit of the X-ray sensing panel 105 are the same as those of the first embodiment. However, the present embodiment differs from the first embodiment in that each pixel of the present embodiment has an electronic shutter function for performing batch exposure.

In the following, a batch exposure operation will be described.

The MOS transistors for resetting 202 of all of the pixels are tuned on in a batch. Thereby, the signal charges of the photoelectric conversion elements 203 are initialized (reset). At the same time, by turning on the clamp switches 207, the clamp capacitors 206 are clamped at the noise levels at the time of the resetting. After a predetermined period of time for accumulation, the reset noises of the accumulated signals are eliminated by the clamp circuits, and the accumulated signals are stored in the sample and hold circuits. To this point of time, all of the pixels are driven at the same timing. Consequently, signal acquisition and signal read-out can be performed separately from each other. The batch resetting and the sample and hold circuits realize the so-called electronic shutter function.

Next, a signal $\phi O_n$ is output from the vertical shift resister 221 to pixels (not shown) of the first row, and the MOS transistors 211 for vertical output switching are turned on. Thereby, the signal charges accumulated in the sample and hold capacitors 210 are read out to the vertical read-out lines 215. After that, signals $\phi H_1$ to $\phi H_m$ are output from the horizontal shift register 222 in order, the signal charges on the vertical read-out lines 215 are read out to the horizontal read-out line 218 in order.

Successively, signal charges of the second and the third rows are read out. When the signal charges on the last row have been read out, the read-out of all of the pixel units 201 of the X-ray sensing panel 105 is completed.

As described above, in the non-destructive read-out mode, after the read-out of the signal charges in the pixel units 201, the next accumulation is begun without resetting the signal charges in the photoelectric conversion elements 203. That is, the quantities of electric charges do not change before and after the read-out of the pixel units 201, and the photoelectric conversion elements 203 are not influenced by the operation of read-out. The present embodiment performs the evaluation of the optimum exposure by the use of the non-destructive read-out, and reads out image signals at the time when the exposure quantity has reached the optimum exposure quantity, as it will be described later in detail. The present embodiment also performs the detection of the completion of X-ray irradiation by means of the non-destructive read-out. Consequently, if X-ray irradiation ends before the exposure quantity reaches the optimum exposure quantity, image signals are read out at the time of the detection of the termination of the X-ray irradiation. The present embodiment is effective in case of preventing over exposure, in particular, of preventing over exposure in a concerned area. That is, in the present invention, the X-ray irradiation apparatus is separated from the X-ray sensing panel. At the time of sensing, an operator sets the optimum irradiation conditions according to parts to be sensed, but sometimes it is impossible to obtain the optimum conditions in cases of an emergency and the like. In such a case, even if an X-ray is irradiated in a slightly excessive quantity, it is possible to execute sensing under the optimum conditions by means of the configuration and the method of the present embodiment. Moreover, it is possible to prevent the impossibility of using an image due to over exposure caused by unintended excessive irradiation of an X-ray.

FIGS. 9A to 9E are timing charts showing the operations of the X-ray sensing apparatus of the present embodiment. In the following, FIGS. 6 to 8 and 9A to 9E are referred while the concrete operations of the present embodiment are described.

First, FIG. 9A shows an exposure start signal form the exposure switch 103. When the exposure switch 103 is turned on, as shown in FIG. 9A, a signal instructing exposure is supplied to the control unit 102. Moreover, the panel drive switch 107 is turned on separately from the X-ray source. The signal is supplied to the panel drive unit (drive unit) 106 and the drive control circuit 108.

When the panel drive unit 106 receives the start signal, the panel drive unit 106 starts the drive of the X-ray sensing panel 105. FIG. 9C shows an operation of the X-ray sensing panel 105. Reference numerals $A_0$ and $A_1$ denote frame operations in the waiting mode. Reference numerals $B_0$ to $B_n$ denote frame operations of the non-destructive read-out. Moreover, when the drive control circuit 108 detects a start of X-ray irradiation, the drive control circuit 108 supplies a mode switching signal to the X-ray sensing panel 105, and stops the reset operation of the frame which is being read out at this point of time, by instructing the accumulation mode. Because the operations concerning the detection of X-ray irradiation are the same as those of the first embodiment, their descriptions are omitted here.

As for the read-out of the X-ray sensing panel 105, as shown in FIG. 9D, the frame of a frame operation $A_0$ is read out in the waiting mode, in which resetting is performed, and the read-out of the X-ray sensing panel 105 after the next frame, in which an X-ray is detected, is performed by the frame operations $B_0$, $B_1$, $B_2$, . . . of the non-destructive read-out.

When an X-ray is irradiated, the part pattern recognition circuit 115 calculates the difference between the electric charges in the frame operation $B_2$ of the non-destructive read-out and in the preceding frame operation $B_1$ of the non-destructive read-out at a time of the completion of the frame operation $B_2$, and calculates the accumulation quantity B of each pixel. That is, the output value of the A/D converter 111 in the frame operation $B_1$ of the non-destructive read-out is subtracted from the output value of the A/D converter 111 of the frame operation $B_2$ of the non-destructive read-out to perform the calculation of OUT$(B_2)$–OUT$(B_1)$, and thereby the accumulation quantity B is calculated. The calculation of the accumulation quantity B is performed to all of the pixels. Incidentally, in this case, the calculation of the accumulation quantity B may be performed in the frame operation $B_1$ of the non-destructive read-out. However, the X-ray is unstable at the time of the frame operation $B_1$ of the non-destructive read-out, and accordingly, the calculation of the accumulation quantity B is performed after the X-ray has become stable, by shifting the execution time by a frame.

After calculating the accumulation quantity B of each pixel, the part pattern recognition circuit 115 performs pattern recognition on the basis of the accumulation quantities as shown in FIG. 9E. The reference pattern optimization circuit 116 forms the reference pattern memory 117, as shown in FIG. 7C, on the basis of the pattern recognition results as described before. Moreover, as described above, the reference value generation circuit 110 generates a REF value corresponding to images on the basis of the pattern recognition results of the part pattern recognition circuit 115.

After the forming of the reference pattern memory 117 and the REF value, the multiplier 118 performs the multiplications of the numerical values of the respective pixels of the reference pattern memory 117 and the output values of the A/D converter 111 (i.e. the quantity of electric charges of the respective pixels of the X-ray sensing panel 105) at every frame of the frame operations $B_4$, $B_5$, . . . of the non-destructive read-out. The multiplier 118 outputs the results of the multiplications to the adder 119. The adder 119 adds the multiplied numerical values of the respective pixels as shown in FIG. 7, and outputs the added values to the comparator 109.

The multiplier 118 and the adder 119 perform the processing described above to every frame operation $B_4$, $B_5$, . . . of the non-destructive read-out. As a result, as shown in FIG. 9D, the output of the adder 119 gradually increases.

The comparator 109 compares an output value of the adder 119 with the REF value. As shown in FIG. 9D, when the output value of the adder 119 becomes equal to the REF value or more (output value≧REF value), the comparator 109 outputs a stopping signal of the signal accumulation mode to the drive control circuit 108 to output the image signals. That is, as shown in FIG. 9E, the drive control circuit 108 decides that the exposure quantity has reached an appropriate exposure quantity, and the drive control circuit 108 outputs a low level signal instructing the waiting mode to the X-ray sensing panel 105. Even if an X-ray is continued to be irradiated at this time as shown in FIG. 9B, the radiation sensing apparatus can take in the image of the optimum exposure. Because the image signals are accumulated in a batch to the sample and hold capacitor of each pixel by means of the electronic shutter function, there is no problem even if the X-ray is continued to be irradiated at the time of the waiting mode. Thereby, as shown in FIG. 9C, signal charges are read out from the X-ray sensing panel 105 in the frame operation $A_1$ of the waiting mode, and the image performs the operation of OUT$(A_1)$–OUT$(A_0)$ by the use of the signal charges in the frame operation $A_0$ of a fist frame in the waiting mode and the frame operation $A_1$ of the waiting mode to output the obtained result. Needless to say, these operations are performed to all of the pixels. Thereby, an output corrected by the FPN correction can be obtained, and the image processing circuit 112 displays the sensed image on the monitor 113 by the use of the obtained outputs, and further stores the image in the recording medium 114 as image data. Here, although the example in which the operation of OUT$(A_1)$–OUT$(A_0)$ is performed by the image processing circuit 112 is shown in the present embodiment, the operation may be also executed by a differencing circuit provided in the X-ray sensing panel 105.

By the present embodiment, it becomes possible to detect a start and a stop of X-ray irradiation and obtain the optimum image by means of an X-ray sensing apparatus not being connected with an X-ray irradiation apparatus.

Incidentally, pixel thinning-out read-out, pixel addition read-out, random access read-out only to effective reference positions (positions in which the numerical values of the reference pattern memory 117 are not zero) may be performed to increase the read-out speed at the time of the non-destructive read-out in the case where the signal charge at every pixel is read out from the X-ray panel 105. In particular, even in the random access read-out, because the electric charges do not change before and after the read-out, the subsequent frames are not influenced. This is a feature of the non-destructive read-out. Moreover, because it is enough for the non-destructive read-out during a wait of X-ray irradiation (waiting mode) or during a period for the detection of the end of X-ray irradiation (during the signal accumulation mode) to detect an X-ray, it is unnecessary to read all of the pixels. The read-out of actual sensing after the irradiation of the X-ray has been begun (destructive read-out in the read-out mode), it is considerable to read out, for example, at the maximum resolution, i.e. to read out all of the pixels, or to read out at a decreased resolution by adding every four pixels, or the like. In this case, the read-out method in which the number of pixels to be added in the non-destructive read-out and the number of pixels to be added in the sensed image read-out (including the case where no pixels are added) differ from each other may be adopted.

Incidentally, although a fluorescent substance is used for converting an X-ray to the light such as visible rays in the present embodiment, the conversion may be performed by the use of a general scintillator, i.e. a waveform conversion body. Moreover, even if the fluorescent body is not used, a photoelectric conversion element which detects a radiation directly by itself to generate electric charges may be adopted.

Moreover, although the descriptions are given to the case where an X-ray is used in the present embodiment, radiations such as an α ray, a β ray and a γ ray can be used.

By means of the radiation sensing apparatus described above, a photographer can expose a subject at arbitrary sensing timing.

Moreover, it becomes possible to obtain a radiation image by reading out a subject signal at a high speed response after the completion of exposure. Thereby, because a radiation image can be obtained without increasing noises such as dark currents, a highly precise image can be obtained.

Furthermore, because the radiation sensing apparatus can acquire subject signals without the necessity of the connection with the radiation irradiation apparatus, and without the necessity of the signal exchanges with the radiation irradiation apparatus, the configuration of the radiation sensing apparatus becomes simple, and the work of timing calibration and the like can be removed.

Many widely different embodiment of the present invention may be constructed without departing from the spirit and scope of the present invention. It should be understood that the present invention is not limited to the specific embodiments described in the specification, except as defined in the appended claims.

What is claimed is:

1. A radiation sensing apparatus comprising:

a sensing unit arranged to sense a subject image to be obtained by irradiating a radiation from a radiation source to a subject, said sensing unit being capable of reading out non-destructively;

a detection circuit arranged to detect a start and/or a stop of irradiation of the radiation on a basis of a signal obtained from said sensing unit by the non-destructive read-out; and a drive circuit arranged to control a waiting mode and a signal accumulation mode, wherein in the waiting mode, said drive circuit performs a reset of said sensing unit periodically in the waiting mode, and stops the reset in accordance with detecting the start of the irradiation of the radiation on a basis of the signal obtained by the non-destructive read-out before the reset, and then starts said signal accumulation mode for causing said sensing unit to perform accumulation of a signal to obtain the subject image.

2. A radiation sensing apparatus comprising:

a sensing unit arranged to sense a subject image to be obtained by irradiating a radiation from a radiation source to a subject, said sensing unit being capable of reading out non-destructively;

a detection circuit arranged to detect a start and/or a stop of irradiation of the radiation on a basis of a signal obtained from said sensing unit by the non-destructive read-out; and a drive circuit arranged to control a signal accumulation mode and a read-out mode, wherein said drive circuit starts the read-out mode for reading out a signal from said sensing unit in accordance with detecting the stop of the irradiation of the radiation on a basis of the signal obtained by the non-destructive read-out in the signal accumulation mode for accumulating the signal to obtain the subject image.

3. A radiation sensing apparatus according to claim 1 or 2, further comprising an evaluation circuit arranged to evaluate whether exposure of the irradiation of the radiation is optimum exposure or not, on a basis of the signal obtained from said sensing unit by the non-destructive read-out.

4. A radiation sensing apparatus according to claim 3, wherein said evaluation circuit includes:

a pattern recognition circuit arranged to recognize an image pattern of the signal obtained from said sensing unit by the non-destructive readout;

a weighting circuit arranged to weight the image pattern recognized by said pattern recognition circuit on each pixel basis;

a storage circuit arranged to store numerical values weighted by said weighting circuit;

a multiplication and addition circuit arranged to multiply the signal output from said sensing unit by the numerical values and perform addition of multiplication results; and a comparing circuit arranged to compare an output of said multiplication and addition circuit with a predetermined reference value;

wherein said evaluation circuit evaluates whether the exposure of the irradiation of the radiation is the optimum exposure or not.

5. A radiation sensing apparatus according to claim 1 or 2, wherein said sensing unit includes a plurality of pixels, each of said pixels including a photoelectric conversion unit and an amplification element for amplifying a signal from said photoelectric conversion unit.

6. A radiation sensing apparatus according to claim 5, wherein said amplification element includes a MOS type transistor which forms a source follower amplifier.

7. A radiation sensing apparatus according to claim 1 or 2, wherein said detection circuit includes:

a storage circuit arranged to store a signal obtained from said sensing unit by the nondestructive read-out for one frame;

a differencing circuit arranged to obtain a difference between the signal of a preceding frame stored in said storage circuit and a signal of a subsequent frame; and a comparison circuit arranged to compare a difference output from said differencing circuit with a predetermined reference value;

wherein said detection circuit detects the start and/or the stop of the irradiation of the radiation on a basis of a comparison result of said comparison circuit.

8. A radiation sensing apparatus according to claim 1 or 2, wherein said drive circuit controls the non-destructive read-out in the waiting mode and/or the signal accumulation mode and read-out in the read-out mode so as to perform different addition read-out in which addition numbers are different in each read-out.

9. A radiation sensing apparatus according to claim 1 or 2, wherein the non-destructive read-out is performed by thinning-out read-out of the signal from said sensing unit.

10. A radiation sensing apparatus according to claim 1 or 2, wherein the non-destructive read-out is performed by addition read-out of the signal from said sensing unit.

* * * * *